United States Patent
Gilfeather et al.

(10) Patent No.: US 6,844,928 B1
(45) Date of Patent: Jan. 18, 2005

(54) FIBER OPTIC SEMICONDUCTOR ANALYSIS ARRANGEMENT AND METHOD THEREFOR

(75) Inventors: Glen P. Gilfeather, Del Valle, TX (US); Srikar V. Chunduri, Austin, TX (US); Brennan V. Davis, Austin, TX (US); David H. Eppes, Austin, TX (US); Victoria Bruce, Austin, TX (US); Michael Bruce, Austin, TX (US); Rosalinda M. Ring, Austin, TX (US); Daniel Stone, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 179 days.

(21) Appl. No.: 09/838,717

(22) Filed: Apr. 19, 2001

Related U.S. Application Data

(60) Provisional application No. 60/198,365, filed on Apr. 19, 2000.

(51) Int. Cl.⁷ .............................................. G01N 21/00
(52) U.S. Cl. ................................................... 356/237.5
(58) Field of Search ........................... 356/237.1–237.9; 438/7–16; 324/750–753

(56) References Cited

U.S. PATENT DOCUMENTS

| | | | |
|---|---|---|---|
| 4,683,750 A | * | 8/1987 | Kino et al. .................... 73/606 |
| 6,395,563 B1 | * | 5/2002 | Eriguchi ........................ 438/7 |

* cited by examiner

Primary Examiner—Tu T. Nguyen

(57) ABSTRACT

The operability of light-based semiconductor die analysis is enhanced using a method and arrangement that directs light between a light source and a die. In one example embodiment of the present invention, a light source is directed to a die in a semiconductor analysis arrangement using a fiber optic cable. The analysis arrangement is adapted to use light received via the fiber optic cable to analyze the die. The analysis includes one or more light-based applications, such as stimulating a selected portion of the die with the light and detecting a response therefrom. In this manner, light can be directed to a die in a variety of analysis implementations, such as for analyzing a die in a test chamber.

19 Claims, 3 Drawing Sheets

FIBER OPTIC SEMICONDUCTOR ANALYSIS ARRANGEMENT AND METHOD THEREFOR

RELATED PATENT DOCUMENTS

This Application claims priority for common subject matter to U.S. Provisional Patent Application Ser. No. 60/198,365, filed on Apr. 19, 2000 and entitled "Semiconductor Analysis Arrangement and Method Therefor," which is fully incorporated herein by reference. This application is further related to U.S. patent application Ser. No. 09/838,671, now U.S. Pat. No. 6,700,659, entitled "Semiconductor Analysis Arrangement and method Therefore"; to U.S. patent application Ser. No. 09/838,667, entitled "Semiconductor Analysis Using Thermal Control"; and to U.S. patent application Ser. No. 09/838,672, now U.S. Pat. No. 6,635,839 entitled "Semiconductor Analysis Arrangement and Method Therefor," all of which are filed concurrently herewith.

FIELD OF THE INVENTION

The present invention relates generally to semiconductor device analysis and, more particularly, to devices and arrangements for fiber optic analysis of a semiconductor die.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of these technological advances has been an increase in the complexity of manufacturing of the devices, which has been accompanied by increased pressure to produce consistent and affordable products.

As the manufacturing processes for semiconductor devices and integrated circuits increase in complexity, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

One type of semiconductor analysis involves conveniently directing perturbation, such as laser light, to a semiconductor device under test (DUT). When performing such analysis, however, there are many issues to be managed. These issues include concerns such as laser leakage, calibration problems, and functional deficiencies. Further, there is a need for convenient approaches to presenting various types of perturbation signals to the DUT, which can be particularly challenging when the analysis of the DUT is to be performed in a chamber or other arrangement that makes access to the DUT difficult.

SUMMARY OF THE INVENTION

The present invention is directed to an approach for semiconductor analysis that improves the efficiency of the analysis. The present invention is exemplified in a number of implementations and applications, some of which are summarized below.

The present invention is directed to addressing needs discussed above and is further useful in connection with the example embodiments disclosed in the above-referenced patent documents. According to an example embodiment of the present invention, a system for analyzing a semiconductor die includes a fiber optic cable adapted to direct light for die analysis. The system includes a light source and a fiber optic cable adapted to receive light from the source. A semiconductor die is held in an analysis arrangement, and light from the light source is directed via the fiber optic cable to perturb the die. In this manner, light can be directed to a die in a variety of applications, such as in a test chamber or in other arrangements where access to the die is challenging.

In a more particular example embodiment of the present invention, the semiconductor die is placed on a stage in a vacuum chamber and the light source is located outside of the chamber. A fiber optic cable extends from the light source and into the chamber. A vacuum is drawn on the chamber, and light from the light source is directed into the chamber via the fiber optic cable. The light is directed to a portion of the die that is to be stimulated using a light direction arrangement, such as a series of mirrors and positioning devices (e.g., servo motors coupled to one or more of: the mirrors, the fiber optic cable and the stage).

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
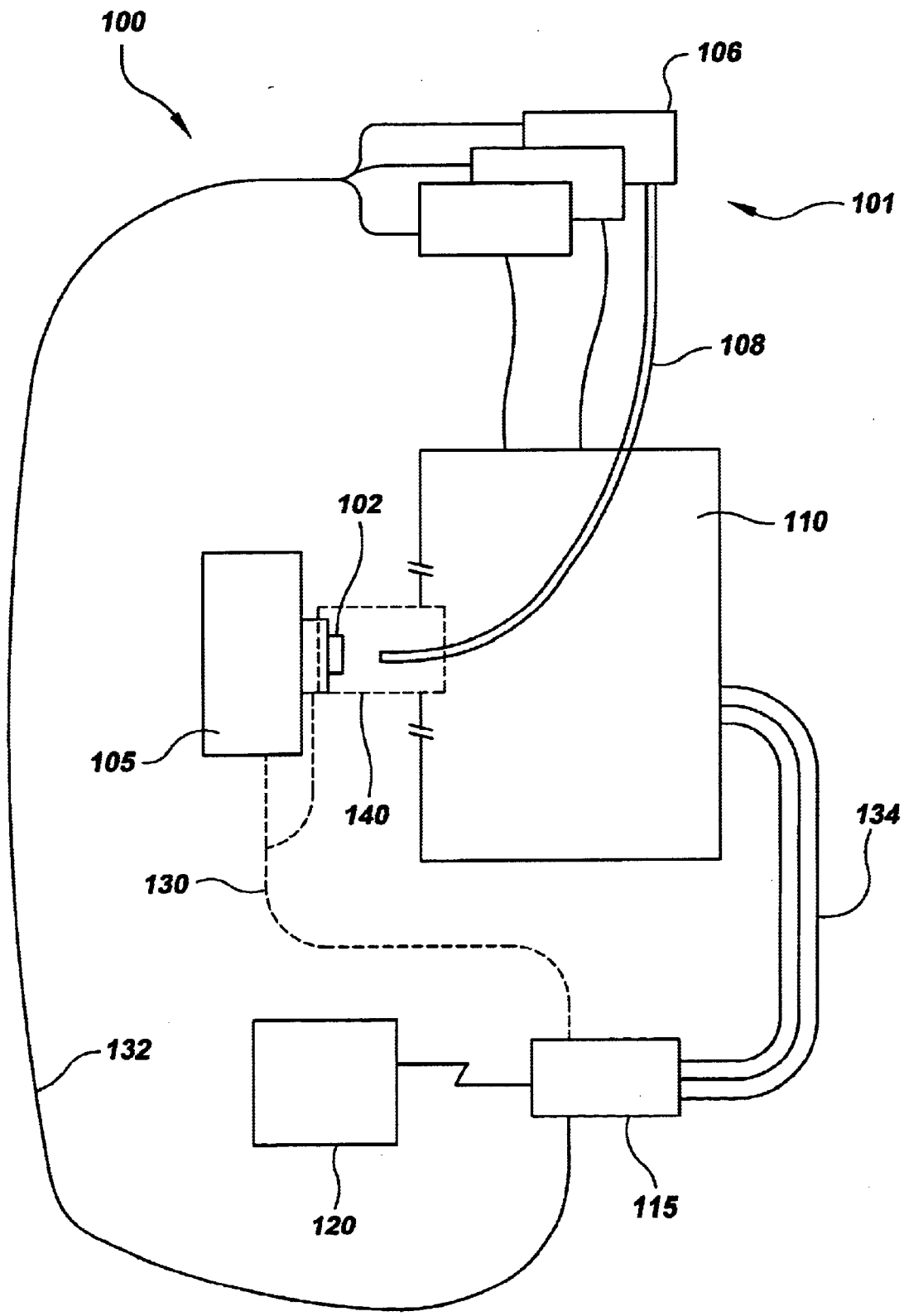
FIG. 1 is semiconductor analysis system, according to an example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of analysis, and the invention has been found particularly suited for die analysis involving light perturbation of the die. While the present invention is not necessarily limited to such devices, various aspects of the invention may be appreciated through a discussion of various examples using this context.

According to an example embodiment of the present invention, a semiconductor die (e.g., DUT) is analyzed using a fiber optic cable to direct light to the die. The die is held in an analysis arrangement, such as a test fixture, a stage or a test chamber. Light is generated at a light source and directed to the die via a fiber optic cable. The light incident upon the die perturbs the die, and the perturbation is used for analyzing the die.

The direction of light via the fiber optic cable is particularly useful for directing light to a selected portion of the die and for directing light to the die in an environment that may not be particularly suited for the generation of light. For example, when the die is in a test chamber, it is sometimes advantageous to maintain the light source outside of the chamber. In this instance, the fiber optic cable allows the light source to be located outside of the test chamber while maintaining the direction of the light to the die in the chamber. The outside location enables access to the light source while the chamber is maintained at a vacuum.

FIG. 1 shows a system 100 for analyzing a semiconductor die 102, according to an example embodiment of the present invention. The system includes a test head 105 adapted to hold the die 102 and to dock with a chamber 110 via a coupling arrangement 140. Once the test head is docked with the chamber, one or more perturbation devices 101, including a light source 106 and other devices, such as a FIB, laser, sonic, microwave, electron beam or ion beam devices is used to analyze the die. Operation control data, such as chamber condition, die response, and other data, is provided to a controller 115. The controller is further adapted to receive response data from the die, such as electrical data obtained from die outputs. The perturbation devices 101 are also optionally coupled to the controller 115, and the controller can be adapted to control and receive feedback from the devices 101. A monitor 120 is coupled to the controller 115 and adapted to display information such as response data, control data. In one particular implementation, the monitor is used as part of an interface for controlling the system 100. For more information regarding the use of a controller in connection with the present invention, reference may be made to U.S. patent application Ser. No. 09/838,672, now U.S. Pat. No. 6,6335,839 entitled "Semiconductor Analysis Arrangement and Method Therefor."

Figure 2:
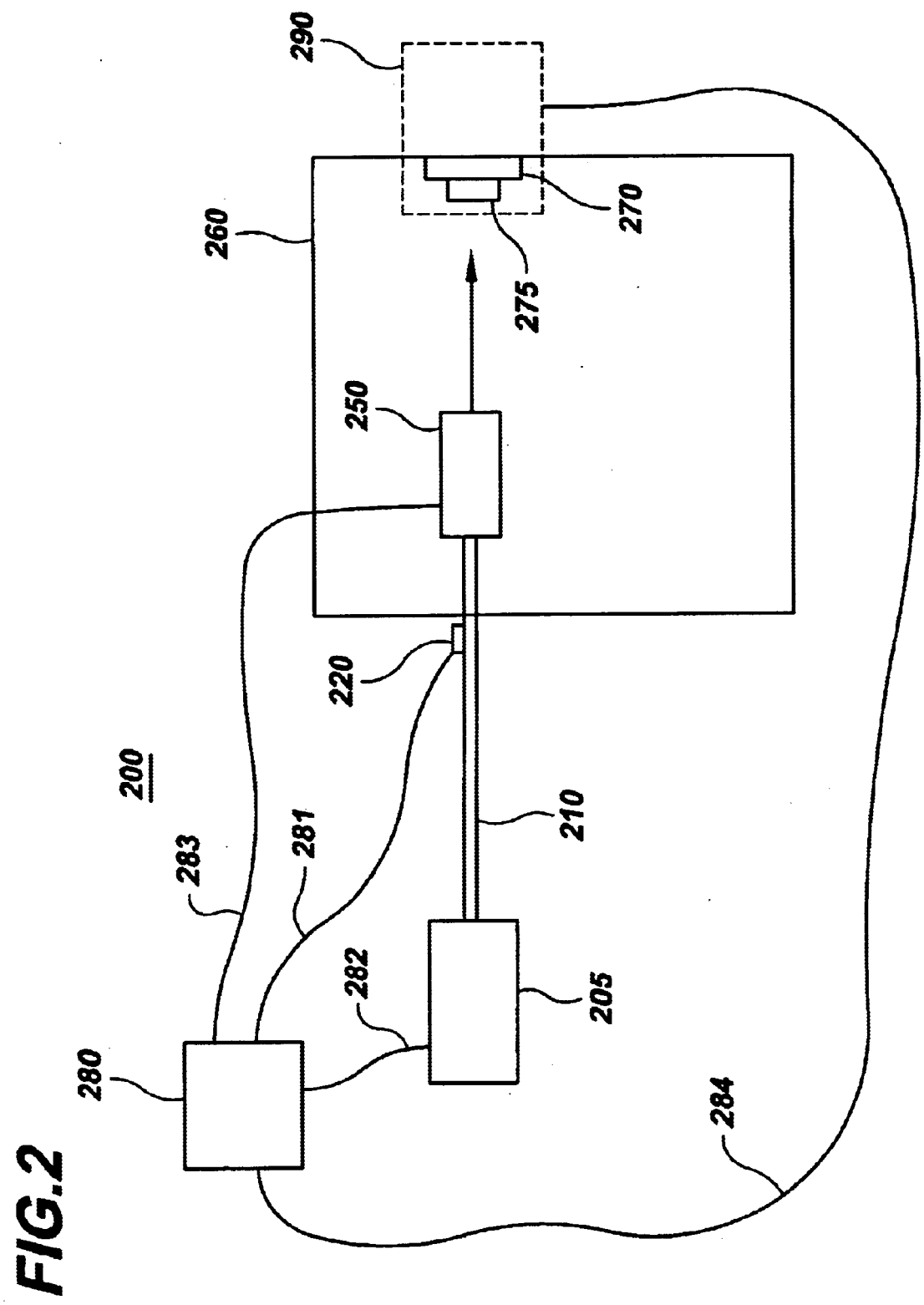
FIG. 2 shows a system adapted to analyze a semiconductor die, according to another example embodiment of the present invention.

In a more particular example embodiment of the present invention, FIG. 2 shows a fiber optic system 200 adapted to analyze a semiconductor die 275. The die is placed on a die holder 270 in a test chamber 260. In one implementation, the holder 270 is part of a docking arrangement 290 adapted to couple to and form a seal with the test chamber 260. A light source 205 generates light and the generated light is directed to the die 275 via a fiber optic cable 210 and a die analysis arrangement 250. In one implementation, the die analysis arrangement 250 is adapted to direct the light to a selected portion of the die using, for example, a series of mirrors and positioning devices (e.g., servo motors coupled to one or more of: the mirrors, the fiber optic cable and the stage). The selected portion is stimulated, and a response from the die is detected. The response may include, for example, an electrical response that can be detected via a connection to the die, or an emission from the die, such as light and/or electrons. In one particular implementation, the die analysis arrangement 250 includes a detector adapted to detect such an emission, and in another implementation (not shown), a separate detector is located in the test chamber 260.

In another example embodiment of the present invention, a photodiode 220 is coupled to the fiber optic cable 210, is communicatively coupled to a controller 280 via communications link 281 and is adapted to detect light leakage from the cable. In response to an amount of light that might leak from the cable, the photodiode generates a signal that is sent to the controller 280. The controller receives the signal and uses it for controlling the analysis of the semiconductor die 275. By detecting light leaking from the fiber optic cable, the corresponding response from the die can be more accurately analyzed because the amount of light incident upon the die can be detected and/or estimated. Any corresponding change in the stimulation or response to the amount of light is accounted for using the detected leakage. In addition, undesirable leakage levels can be avoided. For more information regarding the detection of light leakage, reference may be made to U.S. patent application Ser. No. 09/838,671, now U.S. Pat. No. 6,700,659 entitled "Semiconductor Analysis Arrangement and Method Therefor."

In another example implementation of the present invention (not shown), a photodiode is located inside the chamber 260. This is useful for various applications including those that benefit from the ability to detect light leakage within the chamber without necessarily accessing the inside of the chamber. For instance, one application involves drawing a vacuum on the chamber during die analysis. If the chamber needs to be opened, the vacuum is lost. By placing the photodiode inside the chamber, calibration, safety and other aspects of the light delivery through the fiber optic cable can be realized without necessarily opening the chamber and breaking the vacuum. This makes possible the analysis of a die under vacuum while realizing the benefits of monitoring the light delivery concurrently with the analysis.

The present invention is adaptable for types of analysis including light induced voltage alteration (LIVA), thermal induced voltage alteration (TIVA), optical beam induced current (OBIC) and critical timing path (CTP) analysis. For more information regarding example types of analysis that can be performed in connection with the present invention, reference maybe made to U.S. Pat. No. 5,430,305, filed on Apr. 8, 1994 and entitled "Light-induced Voltage Alteration for Integrated Circuit Analysis," to U.S. Pat. No. 5,523,694, filed on Jun. 4, 1996 and entitled "Integrated Circuit Failure Analysis by Low-energy Charge-induced Voltage Alteration," to U.S. Pat. No. 5,844,416, filed on Nov. 2, 1995 and entitled "Ion-beam Apparatus and Method for Analyzing and Controlling Integrated Circuits," to U.S. patent application Ser. No. 09/259,542, now U.S. Pat. No. 6,177,989 filed on Mar. 1, 1999 and entitled "Laser Induced Current for Semiconductor Defect Detection," and to U.S. patent application Ser. No. 09/385,775, now U.S. Pat. No. 6,541,987 filed on Aug. 30, 1999 and entitled "Laser-excited Detection of Defective Semiconductor Device," which are fully incorporated herein by reference.

Figure 3:
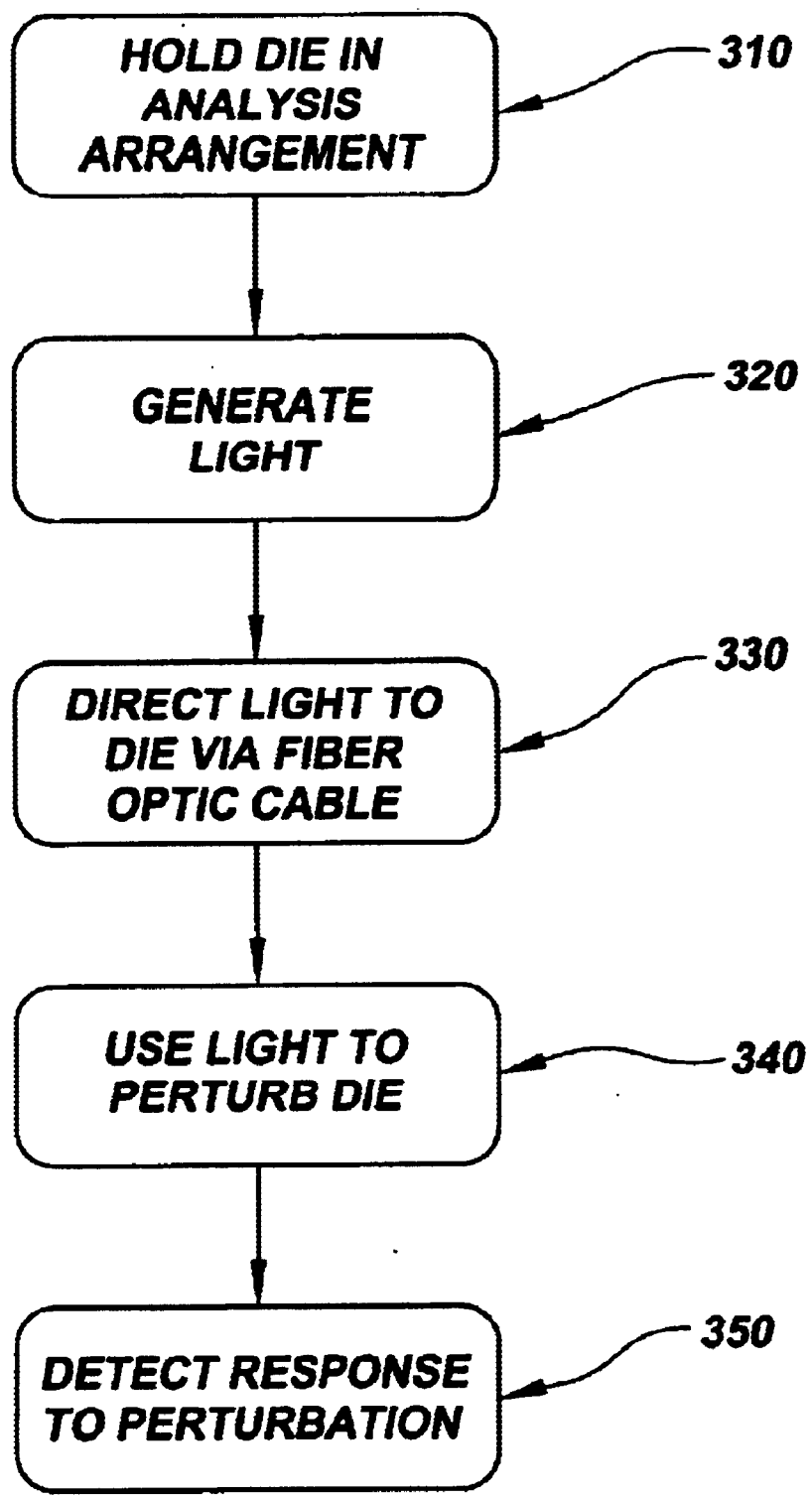
FIG. 3 is a flow diagram of a method for analyzing a semiconductor die, according to another example embodiment of the present invention.

FIG. 3 is a flow diagram of a method for analyzing a semiconductor device, according to another example embodiment of the present invention. The die is placed into and held in an analysis arrangement at block 310. Light is generated at block 320, and the generated light is directed to the held die via a fiber optic cable at block 330. In one implementation, a positioning arrangement is used to direct light from the fiber optic cable to a selected portion of the die. For example, a transistor in the die can be stimulated using a positioning arrangement having a reference for the location of the transistor. The light perturbs the die at block 340, and a response to the perturbation is detected at block 350.

While the present invention has been described with reference to several particular example embodiments, those skilled in the art will recognize that many changes may be made thereto without departing from the spirit and scope of the present invention, which is set forth in the following claims.

What is claimed is:

1. A system adapted to analyze a semiconductor die, the system comprising:
   a light source;
   a semiconductor analysis arrangement adapted to hold a semiconductor die and to use light from the light source to perturb the die for analyzing the die; and
   a fiber optic cable coupled between the light source and the analysis arrangement and adapted to direct light from the light source to the die in the analysis arrangement.

2. The system of claim 1, further comprising a light direction arrangement adapted to direct light from the fiber optic cable to a selected portion of the die.

3. The system of claim 1, wherein the light source includes a laser source.

4. The system of claim 1, wherein the semiconductor analysis arrangement includes a test chamber having a fixture adapted to hold the semiconductor die.

5. The system of claim 4, wherein the analysis arrangement is adapted to evacuate the test chamber.

6. The system of claim 5, wherein the light source is located outside of the test chamber, and wherein the fiber optic cable extends from the light source and into the test chamber.

7. The system of claim 1, further comprising a controller adapted to control the semiconductor analysis arrangement.

8. The system of claim 7, wherein the controller includes a computer.

9. The system of claim 1, wherein the fiber optic cable includes a primary fiber optic waveguide surrounded by a protective fiber optic waveguide.

10. The system of claim 1, wherein the fiber optic cable extends into the analysis arrangement and is adapted to direct light to a semiconductor die held in the analysis arrangement.

11. The system of claim 1, wherein the analysis arrangement includes a detection arrangement adapted to detect a response from the die to the light.

12. The system of claim 11, wherein the detection arrangement is adapted to detect a failure condition of the die.

13. The system of claim 1, farther comprising at least one perturbation device in addition to the light source, the perturbation device adapted to perturb the die.

14. A system adapted to analyze a semiconductor die, the system comprising:
   means for generating light;
   means for holding a semiconductor die and using the generated light to perturb the die for analyzing the die; and
   a fiber optic cable coupled between the means for generating light and the means for holding a semiconductor die and adapted to direct light from the means for generating light to the means for holding a semiconductor die.

15. A method for analyzing a semiconductor die, the method comprising:
   generating light;
   directing the generated light to a die analysis arrangement via a fiber optic cable; and
   holding a semiconductor die and using the generated light to perturb the die for analyzing the die.

16. The method of claim 15, wherein generating light includes generating laser light.

17. The method of claim 15, wherein using the generated light for analyzing the die includes directing the generated light to a selected portion of the die and stimulating the selected portion, further comprising detecting a response from the die to the stimulation and using the response to detect a characteristic of the die.

18. The method of claim 17, wherein using the response to detect a characteristic of the die includes detecting a cause of a failure of the die.

19. The method of claim 15, further comprising placing the die in a vacuum chamber and drawing a vacuum on the chamber, wherein holding the die includes holding the die in the chamber, wherein generating light includes generating light outside of the vacuum chamber and wherein directing the generated light to a die analysis arrangement via a fiber optic cable includes directing the generated light via a fiber optic cable extending into the vacuum chamber.

* * * * *

UNITED STATES PATENT AND TRADEMARK OFFICE
CERTIFICATE OF CORRECTION

PATENT NO. : 6,844,928 B1
DATED : January 18, 2005
INVENTOR(S) : Gilfeather et al.

It is certified that error appears in the above-identified patent and that said Letters Patent is hereby corrected as shown below:

Column 1,
Line 13, "Method Therefore" should read -- Method Therefor --.

Column 3,
Line 38, "6,6335,839" should read -- 6,635,839 --.

Column 6,
Line 1, "farther" should read -- further --.

Signed and Sealed this

Twenty-eighth Day of June, 2005

JON W. DUDAS
*Director of the United States Patent and Trademark Office*